US012629038B2

(12) United States Patent
Davies et al.

(10) Patent No.: US 12,629,038 B2
(45) Date of Patent: May 19, 2026

(54) DEVICE FOR HUMAN PERFORMANCE ASSESSMENT AND MONITORING

(71) Applicant: PREDICOR LLC, Bratenahl, OH (US)

(72) Inventors: Evan V. Davies, Knoxville, TN (US); Michael C. Clark, Silver Spring, MD (US); Michael B. Johnson, Sebring, OH (US)

(73) Assignee: PREDICOR LLC, Bratenahl, OH (US)

(*) Notice: Subject to any disclaimer, the term of this patent is extended or adjusted under 35 U.S.C. 154(b) by 274 days.

(21) Appl. No.: 17/398,111

(22) Filed: Aug. 10, 2021

(65) Prior Publication Data

US 2022/0047174 A1    Feb. 17, 2022

Related U.S. Application Data

(60) Provisional application No. 63/064,153, filed on Aug. 11, 2020.

(51) Int. Cl.
| | |
|---|---|
| *A61B 5/01* | (2006.01) |
| *A61B 5/00* | (2006.01) |
| *A61B 5/0205* | (2006.01) |
| *A61B 5/11* | (2006.01) |
| *G01K 13/00* | (2021.01) |
| *G01P 15/18* | (2013.01) |

(52) U.S. Cl.
CPC ........ *A61B 5/02055* (2013.01); *A61B 5/1118* (2013.01); *A61B 5/6832* (2013.01); *G01K 13/00* (2013.01); *G01P 15/18* (2013.01); *A61B 2560/0252* (2013.01); *A61B 2562/0219* (2013.01)

(58) Field of Classification Search
CPC . A61B 5/01; A61B 5/1118; A61B 2560/0252; G01K 13/00
See application file for complete search history.

(56) References Cited

U.S. PATENT DOCUMENTS

| | | | |
|---|---|---|---|
| 2017/0043215 A1* | 2/2017 | Peterson | G06V 40/23 |
| 2017/0181825 A1* | 6/2017 | Hunter | A61B 5/0031 |
| 2018/0317790 A1* | 11/2018 | Suzuki | A61B 5/02444 |
| 2019/0298183 A1* | 10/2019 | Burg | A61B 5/6814 |
| 2020/0321793 A1* | 10/2020 | Al-Ali | A61B 5/0006 |
| 2021/0330216 A1* | 10/2021 | Azevedo | A61B 5/02438 |
| 2021/0353227 A1* | 11/2021 | Vorster | A61B 5/266 |

* cited by examiner

*Primary Examiner* — Daniel L Cerioni
(74) *Attorney, Agent, or Firm* — Jacob M. Ward; Ward Law Office LLC

(57) ABSTRACT

A wearable device for monitoring physiological and biomechanical parameters of a user includes a primary electronics body having a processor, a first temperature sensor, and a second temperature sensor. The first temperature sensor is in electrical communication with the processor and configured to measure a temperature of skin of the user. The second temperature sensor is in electrical communication with the processor and is configured to measure a temperature of ambient air outside the wearable device. The processor is configured to receive the measured temperatures from the first temperature sensor and the second temperature sensor, and to determine at least one metric indicative of the core temperature of the user without an invasive measurement of the body of the user.

20 Claims, 6 Drawing Sheets

DEVICE FOR HUMAN PERFORMANCE ASSESSMENT AND MONITORING

CROSS-REFERENCE TO RELATED APPLICATIONS

This application claims priority to and the benefit of U.S. Provisional Application No. 63/064,153, filed on Aug. 11, 2020. The entire disclosure of the above application is hereby incorporated herein by reference.

FIELD

The present disclosure relates to monitoring devices and, more particularly, to personal health monitoring devices.

BACKGROUND

The statements in this section merely provide background information related to the present disclosure and may not constitute prior art.

Increasing consumer interest in personal health has resulted in the development of a variety of personal health monitoring devices. Such devices have tended to be complicated to use or are typically designed for use with only one activity such as running or bicycling, for example, but not both or more than one activity. Furthermore, such devices do not provide comprehensive details about workload of a user.

Relatively recent advances in the miniaturization of sensors, power sources, and other electronics or components have enabled personal health monitoring devices to be offered in smaller sizes, form factors, or shapes than were previously feasible or industrially practical. Due to the smaller form factors, many providers are offering personal health monitoring devices that are strapped to the wrist or to the chest of the user. For example, the FITBIT VERSA LITE EDITION™ smartwatch, commercially available from Fitbit LLC in San Francisco, California, is a biometric monitoring device and smartwatch that is strapped to the wrist of the user like a traditional watch.

Undesirably, the known personal health monitoring devices that are strapped to the wrist or to the chest of the user are prone to shifting their position during strenuous athletic activities. This unintentional shifting may result in inaccurate data collection, such as inaccurate acceleration data.

One possible solution to this identified issue is use of an adhesive to militate against the unintentional shifting. Traditionally, electrodes and other commercial devices have utilized an acrylate-based adhesive to be removably affixed to the user. However, undesirably, acrylate-based adhesives have been found to cause deleterious reactions to the stratum corneum, i.e., the outermost layer of the epidermis or surface of the skin, of the user.

There is a continuing need for a wearable monitoring device that militates against unintentional shifting during strenuous athletic activities. Desirably, the multifunctional monitoring device does not use traditional acrylate-based adhesives known to be harmful to the skin of the user.

Furthermore, there is a continued need for a wearable monitoring device that provides a comprehensive detail about the workload of the user, including predicting core body temperature non-invasively.

SUMMARY

In concordance with the present disclosure, a wearable device for measuring physiological and biomechanical parameters of a user to continuously monitor a large number of metrics from a single device, which militates against unintentional shifting during strenuous athletic activities, which does not use traditional acrylate-based adhesives known to be harmful to the skin of the user, and which provides a comprehensive detail about the workload of the user including predicting core body temperature non-invasively, is surprisingly discovered.

It should be appreciated that the technology of the present disclosure is applicable to many different end users. Non-limiting examples include "weekend warriors," patients, healthcare professionals, athletes, law enforcement officers, firefighters, armed forces service members, and industrial workers. Other suitable uses and associated end users of the technology are also contemplated and considered to be within the scope of the present disclosure.

In one embodiment, a wearable device includes a primary electronics body having a processor, a first temperature sensor, and a second temperature sensor. The first temperature sensor is attached to the primary electronics body and in electrical communication with the processor. The first temperature sensor is configured to measure a first temperature, namely, a temperature of skin of the user. The second temperature sensor is configured to measure a second temperature, namely, a temperature of ambient air outside the wearable device. The processor is configured to receive the first temperature from the first temperature sensor, and to receive the second temperature from the second temperature sensor. In operation, the processor is configured to determine at least one metric indicative of the core temperature of the user from the first temperature and the second temperature measured by the first temperature sensor and the second temperature sensor, respectively.

In one example, the wearable device further comprises an accelerometer in electrical communication with the processor. The accelerometer determines at least one of a position, orientation, and motion of the user. The processor calculates impact forces, a number of steps taken, and an external workload via the rate of change of acceleration as determined by the accelerometer, in operation.

In another example, the wearable device further includes an electrocardiogram (ECG) sensor in electrical communication with the processor. The ECG sensor may be configured to detect electrical changes of a heart of the user. In operation, the processor calculates heart rate, respiration rate, resting heart rate, and heart rate variability from the electrical changes of the heart of the user.

In yet another example, both the accelerometer and the ECG sensor are attached to the primary electronics body. In particular, the accelerometer may be attached to a center of the primary electronics body. The accelerometer is configured to determine at least one of a position, orientation, and motion of the user, and the ECG sensor is configured to detect the electrical changes of the heart of the user. The processor calculates physiological and biomechanical parameters from data collected by the accelerometer and the ECG sensor, in operation.

In various other examples, the primary electronics body is either a fully flexible circuit board, a rigid circuit board, or a combination of a flexible and rigid circuit board.

The wearable device may further have a biocompatible adhesive disposed on a bottom side of the primary electronics body. The primary electronics body or housing is thereby configured to be removably affixed to the user. In particular, the biocompatible adhesive may be a silicone-acrylate-based adhesive.

In a further example, a wearable device includes a primary electronics body having electronic components including a processor, a housing configured to enclose the electronic components, a first temperature sensor attached to the primary electronics body in electrical communication with the processor and configured to measure a temperature of skin of the user, and a second temperature sensor in electrical communication with the processor and configured to measure a temperature of ambient air outside the wearable device. The processor is configured to receive the first temperature from the first temperature sensor and the second temperature from the second temperature sensor, and to determine at least one metric indicative of the core temperature of the user from the first temperature and the second temperature.

In another embodiment, a wearable device includes a primary electronics body having electronic components including a processor, a housing configured to enclose the electronic components, a first temperature sensor, and a biocompatible adhesive. The first temperature sensor is attached to the primary electronics body and in electrical communication with the processor. The first temperature sensor is configured to measure a first temperature, namely, a temperature of skin of the user. The biocompatible adhesive is disposed on a bottom side of at least one of the primary electronics body and the housing. The housing or the primary electronics body is thereby configured to be removably affixed to the user. In particular, the biocompatible adhesive may be a silicone-acrylate-based adhesive. The processor is configured to receive the first temperature from the first temperature sensor. In operation, the processor is configured to determine at least one metric indicative of the core temperature of the user from the first temperature sensor.

In one example, the wearable device further comprises an accelerometer in electrical communication with the processor. The accelerometer determines at least one of a position, orientation, and motion of the user. The processor calculates impact forces, a number of steps taken, and an external workload via the rate of change of acceleration, in operation.

In another example, the wearable device further includes an ECG sensor in electrical communication with the process. The ECG sensor is configured to detect electrical changes of the heart of the user. In operation, the processor calculates heart rate, respiration rate, resting heart rate, and heart rate variability from the electrical changes of the heart of the user.

In another example, the wearable device further includes both the accelerometer and the ECG sensor attached to the primary electronics body. In particular, the accelerometer may be attached to a center of the primary electronics body. The accelerometer determines at least one of a position, orientation, and motion of the user. The ECG sensor is configured to detect electrical changes of the heart of the user. The processor calculates physiological and biomechanical parameters from data collected by the accelerometer and the ECG sensor, in operation.

In other various examples, the primary electronics body is either a fully flexible circuit board, a rigid circuit board, or a combination of a flexible and rigid circuit board.

In yet other examples, the wearable device further has a second temperature sensor. The second temperature sensor is configured to measure a second temperature, namely, a temperature of ambient air outside the wearable device.

In a further embodiment, a wearable device for monitoring physiological and biomechanical parameters includes a housing, a primary electronics body, and a plurality of electronic components. The electronic components are electrically connected to the primary electronics body. The plurality of electronic components includes a processor, and a memory that stores a program to be executed by the processor. The wearable device further includes a first temperature sensor in electrical communication with the processor. The first temperature sensor is configured to measure a first temperature, namely, a temperature of skin of the user. The wearable device also has a second temperature sensor in electrical communication with the processor. The second temperature sensor is configured to measure a second temperature, namely, a temperature of ambient air outside the wearable device. The wearable device also has an ECG sensor in electrical communication with the processor. The ECG sensor is configured to detect electrical changes of a heart of the user. The wearable device further has an accelerometer in electrical communication with the processor. The accelerometer is configured to measure at least one of a position, orientation, and motion of the user. The wearable device further has a biocompatible adhesive disposed on a bottom side of at least one of the primary electronics body and the housing. The primary electronics body or the housing is thereby configured to be removably affixed to the user. In particular, the biocompatible adhesive may be a silicone-acrylate-based adhesive.

In operation, the processor receives signals encoding data or information from the first temperature sensor, the second temperature sensor, the ECG sensor, and the accelerometer. The processor is configured to calculate at least one physiological and biomechanical metric from the data received, and to output at least one metric indicative of the core temperature of the user, for example to a display on the wearable device or on a graphical user interface of another device, such as a smartphone or computer, with which the wearable device is in networked communication. The location, thickness, and type of the biocompatible adhesive is configured to militate against an unintentional shifting of the wearable device on the user in operation.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

Figures 16, 17, 18:
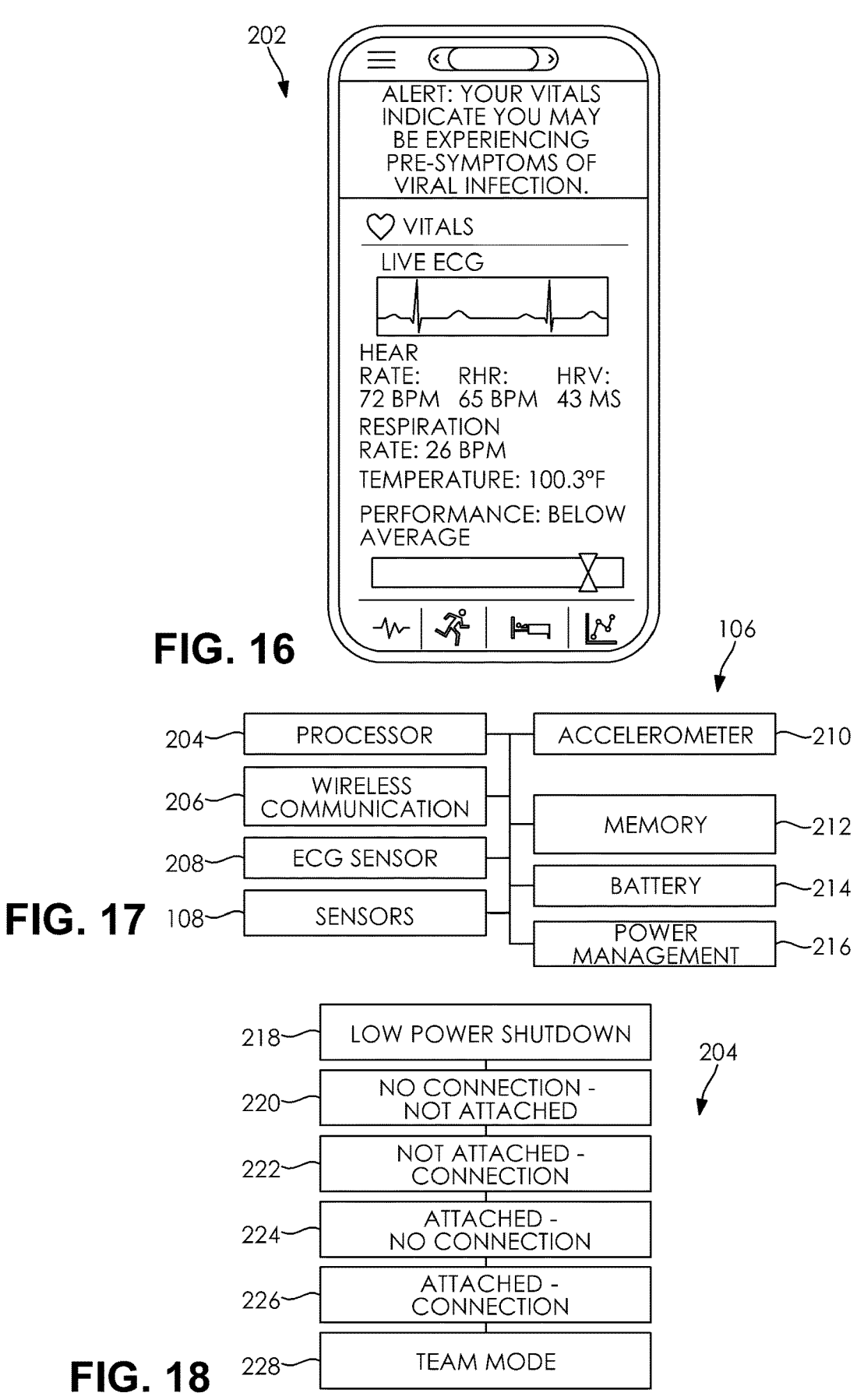
FIG. 16 is a front elevational view of a mobile phone with a graphical user interface (GUI) of an exemplary mobile application that can be used in combination with the wearable device according to the disclosure, the mobile phone being in networked communication with the wearable device.

FIG. 17 is a block diagram illustrating electronics components of the wearable device in electrical communication with the processor of the wearable device according to the present disclosure; and FIG. 18 is a block diagram illustrating various operating modes defined by executable instructions embodied on the memory of the wearable device, and which may be executed by the processor of the wearable device according to the present disclosure.

DETAILED DESCRIPTION

The following description of technology is merely exemplary in nature of the subject matter, manufacture, and use of one or more inventions, and is not intended to limit the scope, application, or uses of any specific invention claimed in this application or in such other applications as can be filed claiming priority to this application, or patents issuing therefrom. Regarding methods disclosed, the order of the steps presented is exemplary in nature, and thus, the order of the steps can be different in various embodiments, including where certain steps can be simultaneously performed.

The terms "a" and "an" as used herein indicate "at least one" of the item is present; a plurality of such items can be present, when possible. Except where otherwise expressly indicated, all numerical quantities in this description are to be understood as modified by the word "about" and all geometric and spatial descriptors are to be understood as modified by the word "substantially" in describing the broadest scope of the technology. The term "about" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that can arise from ordinary methods of measuring or using such parameters.

Although the open-ended term "comprising," as a synonym of non-restrictive terms such as including, containing, or having, is used herein to describe and claim embodiments of the present technology, embodiments can alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application.

Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter can define endpoints for a range of values that can be claimed for the parameter. For example, if Parameter X is exemplified herein to have value A and also exemplified to have value Z, it is envisioned that Parameter X can have a range of values from about A to about Z. Similarly, it is envisioned that disclosure of two or more ranges of values for a parameter (whether such ranges are nested, overlapping, or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X can have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it can be directly on, engaged, connected, or coupled to the other element or layer, or intervening elements or layers can be present. In contrast, when an element is referred to as being "directly on," "directly engaged to," "directly connected to" or "directly coupled to" another element or layer, there can be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. can be used herein to describe various elements, components, regions, layers and/or sections, these elements, components, regions, layers and/or sections should not be limited by these terms. These terms can be only used to distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, can be used herein for ease of description to describe one element or feature's relationship to another element(s) or feature(s) as illustrated in the figures. Spatially relative terms can be intended to encompass different orientations of the device in use or operation in addition to the orientation depicted in the figures. For example, if the device in the figures is turned over, elements described as "below", or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

All documents, including patents, patent applications, and scientific literature cited in this detailed description are incorporated herein by reference, unless otherwise expressly indicated. Where any conflict or ambiguity can exist between a document incorporated by reference and this detailed description, the present detailed description controls.

Referring to FIGS. 1-4, a wearable device 100 is shown for monitoring physiological and biomechanical parameters of a user (not shown). The wearable device 100 comprises a housing 102, a primary electronics body 104, electronic components 106, a plurality of sensors 108, at least one contact 110, and at least one layer of biocompatible adhesive 112.

The housing 102 is configured to enclose and protect the electronic components 106. The housing 102 has a top side 114 and a bottom side 116. The top side 114 forms an outer surface of the wearable device 100 when worn by the user. The bottom side 116 is disposed adjacent to the skin of the user when the wearable device 100 is being used. In certain embodiments, the housing 102 may only have the top side 114 and the primary electronics body 104 will be exposed underneath the housing 102 and configured to be disposed adjacent to the user when the wearable device 100 is worn.

The housing 102 may be formed for any of a variety of materials or combinations of materials, such as for example, a semi-flexible silicone material and/or a water-resistant material that allows the wearable device 100 to be durable and flexible enough to withstand active athletic use for a significant amount of time. It should be appreciated that other durable materials, such as other plastic or rubber materials, may also be employed while remaining within the scope of the present disclosure.

Figures 4, 5, 6:
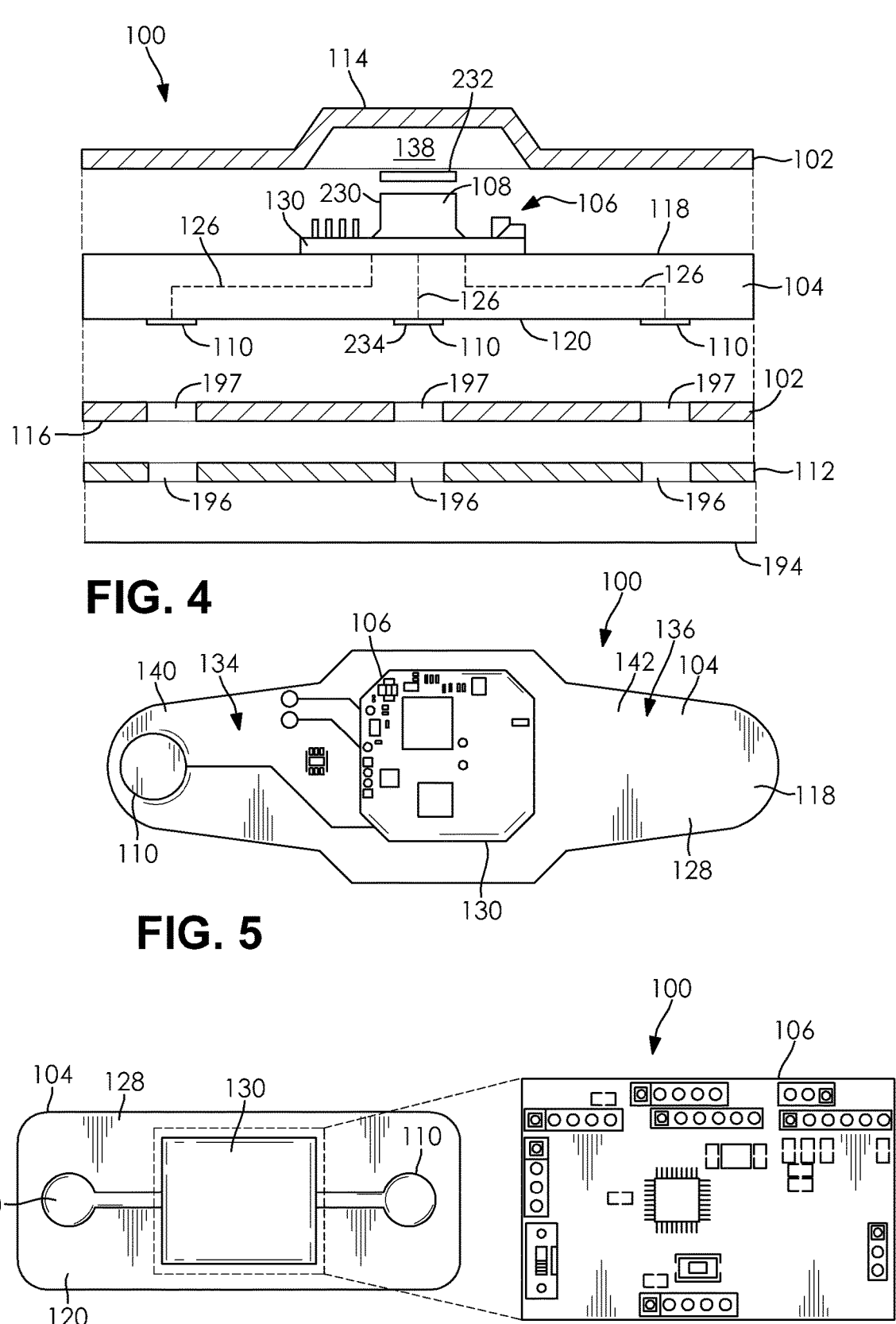
FIG. 4 is an exploded cross-sectional side elevational view of the wearable device taken at section line A-A in FIG. 1.
FIG. 5 is a top plan view of a base of the wearable device with a portion of a housing removed to illustrate a printed circuit board (PCB) having a flexible portion and a rigid portion according to one embodiment of the present disclosure.
FIG. 6 is a bottom plan view of the base of the wearable device illustrating the flexible PCB portion and a rigid PCB portion according to the present disclosure.

Referring to FIG. 4, the primary electronics body 104 may be defined by a printed circuit board (PCB). The primary electronics body 104 has an upper side 118, and a lower side 120. The lower side 120 that is disposed on the primary electronics body 104 opposite the upper side. The upper side 118 may be a components side on which many or all of the electronic components are attached. The upper side 118 of the primary electronics body 104 is configured to engage with an inner surface of the housing 102 to secure the primary electronics body 104 to the housing 102 such that the electronic components 106 are enclosed within the wearable device 100.

The lower side 120 may be oriented toward the stratum corneum (skin) of the user. In other words, the bottom side 116 of the housing 102 and the lower side 120 of the primary electronics body 104 may together form a side of the wearable device 100 that contacts the user in operation. In an alternative embodiment, not shown, the housing 102 may not have the bottom side 116 and the lower side 120 of the primary electronics body 104 may alone form the side of the wearable device 100 that contacts the user in operation.

The at least one contact 110 is disposed on the lower side 120 of the primary electronics body 104 and is in communication with at least one of the plurality of sensors 108. In some instances, the at least one contact 110 is in communication with at least one of the plurality of sensors 108 via a flexible trace, wire, or lead 126, for example, as shown in FIG. 4 The at least one contact 110 is configured to contact the stratum corneum of the user and serve as a measuring area for at least one of the plurality of sensors 108.

In one example, as shown in FIGS. 1-4, the at least one contact 110 is an exposed electrode pad. The exposed electrode pad, in combination with at least one of the plurality of sensors 108, may be configured to detect small electrical changes that are consequence of cardiac muscle depolarization followed by repolarization during each cardiac cycle (heartbeat). This information may be used to produce an electrocardiogram (ECG), which is described in greater detail below.

The primary electronics body 104 may also include electrical leads 126 or other layer conductors for communication between the electronic components 106 and the contact 110. As shown in FIG. 4, the leads 126 may be embedded in the primary electronics body 104, represented by dashed lines. However, it should be appreciated that one skilled in the art may position the leads 126 on upper or lower sides 118, 120 of the primary electronics body 104 while remaining within the scope of this disclosure. The leads 126 may further be covered with a protective encapsulant if positioned on the upper or lower sides 118, 120 of the primary electronics body 104.

Referring to FIGS. 5-6, in certain embodiments the primary electronics body 104 may have a flexible PCB portion 128 and a rigid PCB portion 130. The rigid PCT portion 130 may be disposed at a center 132 of the flexible PCB portion 128, for example. It should be appreciated that the flexible PCB portion 128 may permit for deformation, twisting, bending, and flexing of the primary electronics body 104, thereby allowing the wearable device 100 to conform to the curvatures of a body part of the user, such as a chest of the user, for example, while the rigid PCB portion 130 protects electronic components coupled thereto within the housing 102.

The flexible PCB portion 128 portion may include a first wing 134 disposed on one side of the rigid PCB portion 130 and a second wing 136 disposed on the other side of the rigid PCB portion 130. Without being bound to a particular theory it is believed that this configuration permits the wearable device to conform more to the curvatures of the body part of the user, such as the chest of the user, for example. It should be appreciated that although this configuration has been shown to be useful, other shapes and sizes may be employed for the flexible portion while remaining within the scope of the present disclosure.

In this embodiment, shown in FIGS. 5 and 6, the housing 102 defines a shape corresponding to the primary electronics body 104. Accordingly, the housing 102 defines a central cavity 138 forming a shell that is configured to enclose and protect the electronic components 106. The housing 102 includes a first housing wing 140 and a second housing wing 142 corresponding to the first and second wings 134, 136 of the PCB or primary electronics body 104. The first housing wing 140 is disposed on one side of the central cavity 138 and the second wing 142 is disposed on the other side of the central cavity 138. Where the housing 102 is secured to the primary electronics body 104, the first and second housing wings 140, 142 of the housing 102 align with the first and second wings 134, 136 of the primary electronics body 104, respectively, such that the electronic components 106 utilizing the rigid PCB portion 130 are enclosed within the central cavity 138 of the housing 102.

Referring to FIGS. 7-10, a wearable device 150 according to another embodiment of the present disclosure is illustrated. In this example, the wearable device 150 includes a rigid PCB portion 152 and a flexible PCB portion 154. The flexible PCB portion 154 is defined by a first flexible wing 156 disposed on one side of the rigid PCB portion 152 and a second flexible wing 158 disposed on the other side of the rigid PCB portion 152. The rigid PCB portion 152 is disposed within an electronics housing 160, which is configured to enclose and protect electronic components 162. The electronics housing 160 encapsulates the rigid PCB portion 152; however, the electronics housing 160 does not extend beyond the rigid PCB 152. Accordingly, and unlike the embodiments shown in FIGS. 1-6, much of the flexible PCB portion 154 is not in contact with the housing 160 in the embodiment shown in FIGS. 7-10.

Figures 7, 8, 9, 10:
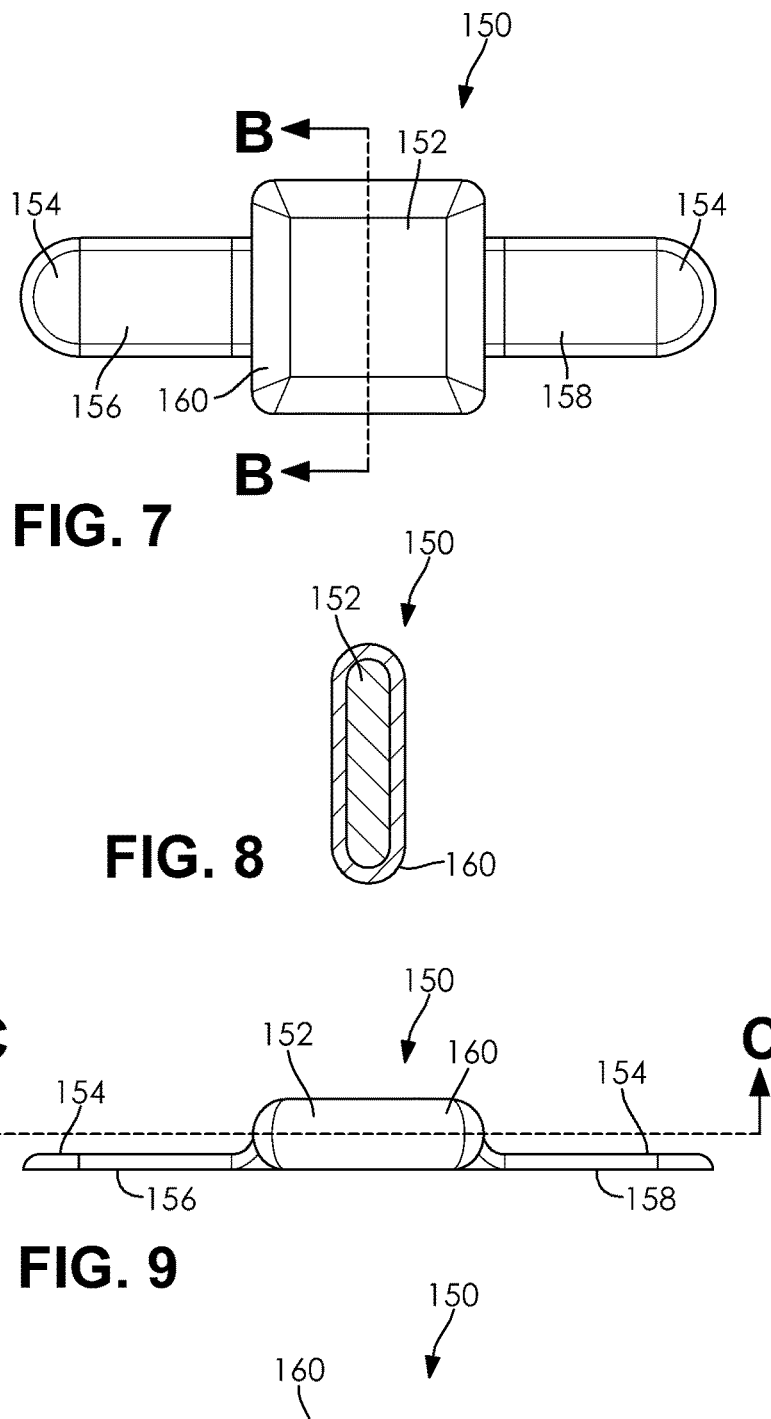
FIG. 7 is a top plan view of a wearable device according to another embodiment of the present disclosure, and illustrating the use of both a rigid PCB and a flexible PCB.
FIG. 8 is a cross-sectional side elevational view of the wearable device taken at section line B-B in FIG. 7.
FIG. 9 is a side elevational view of the wearable device of FIG. 7.
FIG. 10 is a cross-sectional bottom plan view of the multifunctional device taken at section line C-C in FIG. 9, and showing an interior of the housing containing the rigid PCB.

With reference to FIG. 7, it should be appreciated that the dimensions of the wearable device 150 may be selected depending on the desired body part and location of measurement for the end user. For example, the wearable device 150 may have a maximum length and a maximum width, with the maximum length being at least three times the maximum width of the wearable device 150. In specific examples, the maximum length may be around three inches (3") and the maximum width may be around one inch (1"). While these dimensions have shown to be useful, one skilled in the art may select other dimensions within the scope of this disclosure.

With reference to FIGS. 7 and 9, the electronics housing 160 may have a housing length, a housing width, and a housing height. The housing length and the housing width may be selected to be about the same, in certain cases, and may about at least three times the housing height. In specific examples, the housing length may be around one inch (1"), the housing width may be around one inch (1"), and the housing height may be about one-third of an inch (0.31"). However, it should be appreciated that a skilled artisan may employ different but suitable dimensions for the electronic housing, as desired.

The flexible PCB portion 154 may further be flexible in more than one dimension. For example, the flexible PCT portion 154 may have at least one of a flexible length, flexible width, and a flexible height. In specific examples, the flexible length is about two inches (2"). Also, the flexible width is about one-half of an inch (0.50"). In addition, the flexible height is less than about one-tenth of an inch (0.06"). Although these dimensions have shown to be useful, other dimensions may be chosen for the flexible PCB portion 154, as desired.

Figure 11:
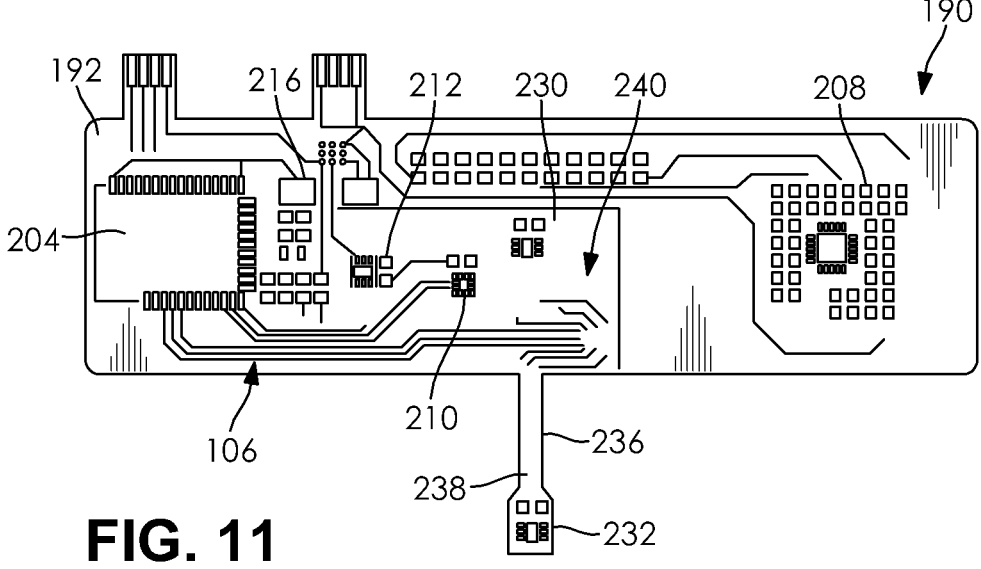
FIG. 11 is a top plan view of the primary electronics body of the wearable device shown in FIG. 7 illustrating the flexible PCB according to another embodiment of the present disclosure.
Figure 12:
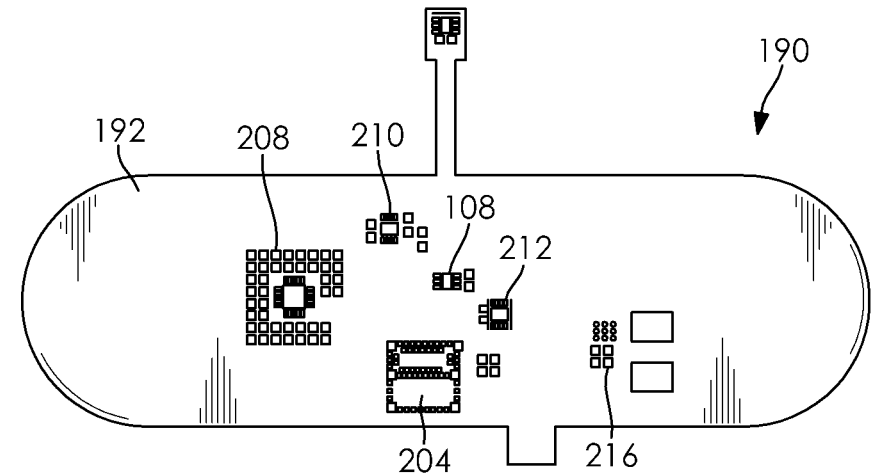
FIG. 12 is a top view of the primary electronics body of the wearable device illustrating the flexible PCB according to yet another embodiment of the present disclosure.

Referring to FIGS. 11-12, a wearable device 190 according to another embodiment of the present disclosure is illustrated. In this form, the wearable device 190 includes a primary electronics body 192 that may be defined by a fully flexible PCB. A geometry of the flexible PCB or primary electronics body 192 may be in the shape of a rectangle (FIG. 11) or a stadium (FIG. 12); however, other shapes may be employed while remaining within the scope of the present disclosure.

Figure 13:
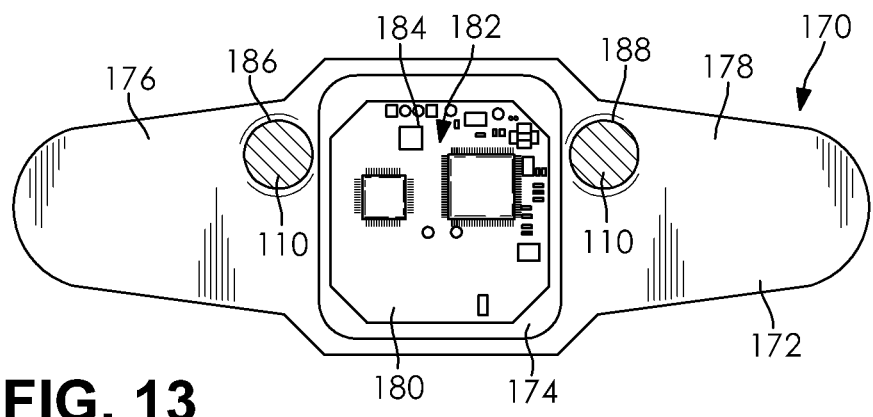
FIG. 13 is a bottom plan view of a wearable device according to yet another embodiment of the disclosure, and illustrating a rigid PCB secured in the housing.

Referring to FIG. 13, a wearable device 170 according to yet another embodiment of the present disclosure is illustrated. The wearable device 170 includes a housing 172 defining a central aperture 174, a first wing 176 disposed on one side of the central aperture 174 and a second wing 178 disposed on the other side of the central aperture 174. The wearable device 170 further includes a rigid PCB 180, electronic components 182 attached to the rigid PCB, and a battery 184 disposed within the central aperture 174 of the housing 172 to protect the battery 184 and rigid PCB 180. Each one of the first and second wings 176, 178 defines an opening 186, 188 having the at least one contact 110 placed adjacent thereto.

With renewed reference to FIG. 4, the at least one layer of biocompatible adhesive 112 is configured to be removably affixed to the body part of the user, such as the chest of the user, in operation. Advantageously, removably affixing the at least one layer of biocompatible adhesive 112 to the chest of the user facilitates the wearable device 100 to remain in substantially the same position on the chest of the user. This may result in more accurate readings from the plurality of sensors 108 since the employment of the biocompatible adhesive 112 militates against the at least one contact 110 losing connection to the stratum corneum (skin) of the user. In addition, the at least one layer of the biocompatible adhesive 112 militates against an unintentional shifting during strenuous athletic activities, unlike traditional wearables that are strapped to the wrist or the chest of the user with belts or bands. It should be appreciated that one skilled in the art may scale the location, type, and dimensions of the layer of biocompatible adhesive 112, as desired.

In specific examples, the at least one layer of the biocompatible adhesive 112 is a silicone-acrylate-based adhesive. Without being bound to a particular theory, it is believed that that the silicone-acrylate-based adhesive alleviates some of the known irritations brought about by some commercial acrylate-based adhesives. Desirably, the silicone-acrylate-based adhesive also facilitates a long-term duration of adhesion to the body part, such as the chest, of the user. It should be appreciated that a skilled artisan may select other biocompatible adhesives, as long as they alleviate some of the known irritations known in commercial adhesives, while remaining within the scope of the present disclosure.

In another example, the at least one layer of the biocompatible adhesive 112 is a double-sided adhesive having a first side removably attached to the wearable device 100 and a second user side configured to be removably affixed to the chest of the user. Suitable silicone-acrylate-based double-sided adhesive may include 2477P™ Double Sided Silicone/Acrylate Thermoplastic Elastomer, commercially available from 3M; however, other suitable types of silicone-acrylate-based adhesives are contemplated and may be selected by one of ordinary skill in the art within the scope of the present disclosure.

It should be appreciated that the biocompatible adhesive 112 may be either permanently affixed or removably affixed to at least one of the housing 102 and the primary electronics body 104, as desired. Where the biocompatible adhesive 112 is removably affixed, the primary electronics body 104 may include fasteners (not shown) for removably holding the biocompatible adhesive 112. Additionally, where removably affixed, it should be appreciated that the biocompatible adhesive 112 may be replaced for repeated use of the wearable device 100 long-term. For example, where removably affixed, the biocompatible adhesive 112 may be removed and replaced before each subsequent use.

Regardless of whether the biocompatible adhesive 112 is permanently or removably affixed, it should be understood that a protective backing 194 (shown in FIG. 4), such as a peel away plastic film may also be employed on the user side until adherence of the wearable device 100 to the skin is desired.

The at least one biocompatible adhesive 112 may also define at least one opening 196 having a geometric shape corresponding to that of the at least one electrode or contact 110. The at least one opening 196 allows the electrode or contact 110 to directly contact the skin, in operation. It should be appreciated that there may at least one corresponding hole 197 also formed in the housing 102, for example, as shown in FIG. 4. The corresponding hole 197 alights with the at least one opening 196 of the adhesive 112 to allow the electrode or contact 110 to be disposed therethrough. The biocompatible adhesive may further incorporate a gel electrode material for use in monitoring vitals in electrocardiogram (ECG) applications, which is described in greater detail below.

As shown in FIGS. 4 and 11, the electronic components 106 are electrically connected to the primary electronics body 104 and coupled to the at least one contact 110 and/or one of the plurality of sensors 108 to measure physiological and biomechanical information for continuous monitoring of a large number of metrics from a single device.

Figures 14, 15:
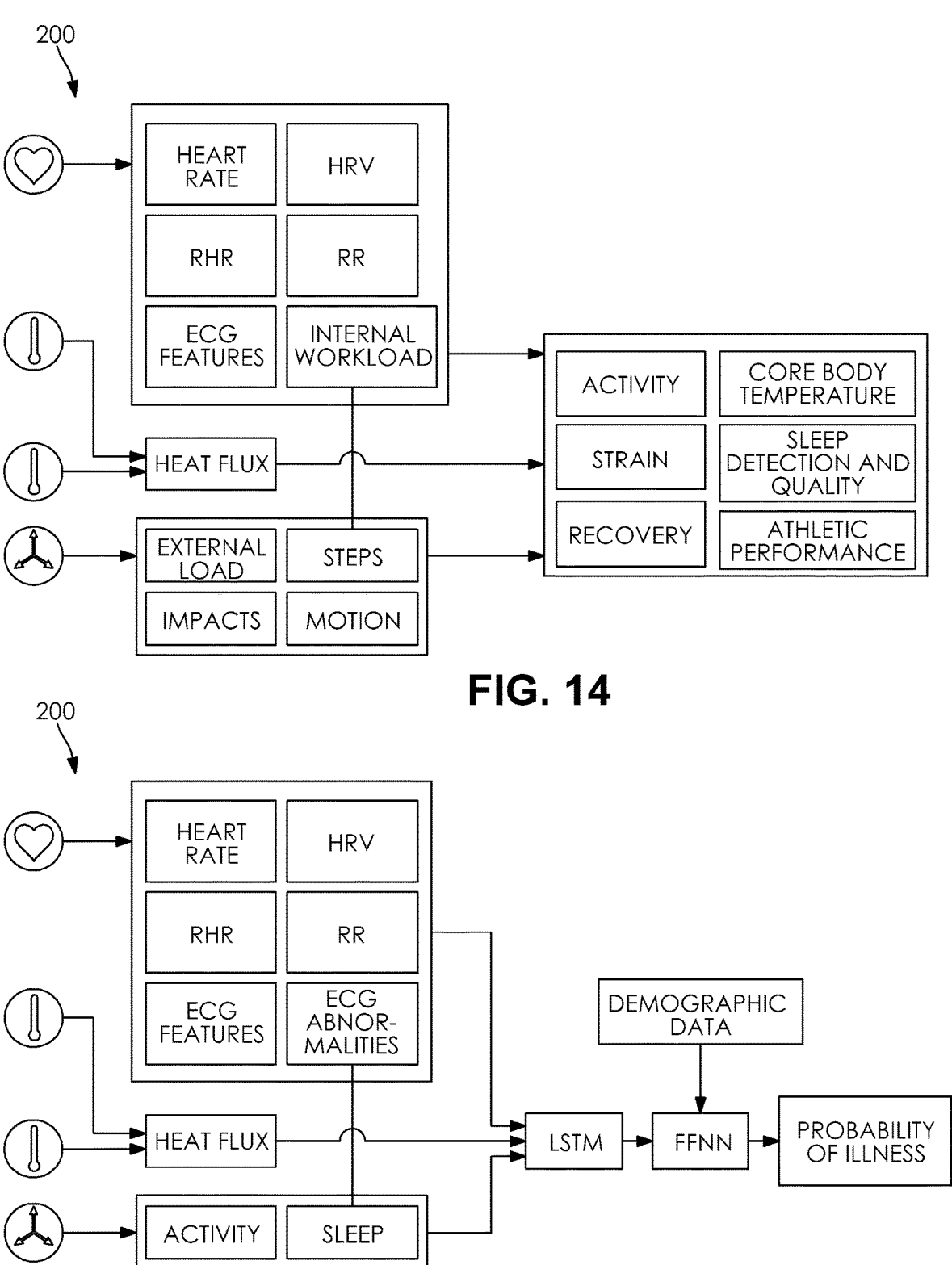
FIG. 14 is a schematic diagram illustrating various useful processes defined by executable instructions embodied in a memory of the wearable device according to certain embodiments of the disclosure, and which may be executed by the processor of the wearable device according to the present disclosure to inform the user on athletic performance and recovery.
FIG. 15 is a schematic diagram illustrating various useful processes defined by executable instructions embodied in a memory of the wearable device according to additional embodiments of the disclosure, and which may be executed by the processor of the wearable device according to the present disclosure to inform the user on detection of illness.

Referring to FIGS. 14-15, the wearable device 100, 150, 170, 190 may utilize an analytical software platform 200. The analytical software platform 200 is configured to convert the raw physiological and biomechanical measurements into relevant metrics for the user. Non-limiting examples of the relevant metrics includes at least one of heart rate (HR), respiration rate (RR), heart rate variability (HRV), resting heart rate (RHR), ECG features, skin temperature, ambient temperature, heat flux, acceleration in X, Y, Z axes, impacts, steps, external workload, sleep, activity, recovery, motion profiling, cardiovascular strain, internal workload, athletic performance, core body temperature, and the probability of infection or overall wellness. Examples of the ECG features may include, but are not limited to, PQRST and U wave location, amplitude, phase and area, and time difference and length of all waves and wave complexes, for example, QRS, QT interval, and PQ interval, among others.

It should be appreciated that the relevant metrics may include also include other information relevant to the health of the user, as desired.

The analytical software platform 200 may be defined by processor-executable instructions stored on a memory of the wearable device 100, 150, 170, 190. In other instances, the analytical software platform 200 is a part of a separate application 202 on a mobile device (shown in FIG. 16) or networked computer that is used in combination with the wearable device 100, 150, 170, 190. Non-limiting examples of the separate application may include a web app, a dedicated application, or a mobile application. It should be appreciated that the software may take the form of other types of applications, within the scope of this disclosure.

The analytical software platform 200 is also configured to perform several different processes with data collected by the wearable device 100, 150, 170, 190 such as, but not limited to, data collection, signal processing, and use of early detection algorithms. The early detection algorithms may be utilized to calculate the probability of infections. Desirably, this may allow users to identify illnesses and other infections within their bodies before symptoms occur.

In specific examples, as shown in FIG. 15, the analytical software platform 200 may further include neutral networks such as Long Short-Term Memory (LSTM) networks. LTSM networks are configured to facilitate recognizes long term dependences. Advantageously, this allows LSTM networks to assist in predicting the outcome of a sequence of time dependent data. It should be appreciated that a skilled artisan may employ other structure and features within the analytical software platform 200, such a feedforward neural network (FFNN), machine learning, and artificial intelligence (AI), as desired.

Referring to FIGS. 11 and 17, the electronic components 106 include a processor 204, at least one wireless communication protocol 206, an ECG sensor 208, the plurality of sensors 108, an accelerometer 210, a memory 212, a battery 214 and a power management system 216.

Other electronic components such as transmitters, receivers, or transceivers (not shown) for transmission and receipt of wireless radio signals may also be provided in communication with the processor 204. For example, the processor 204 in communication with the transceiver is capable of processing, receiving, and transmitting data or instructions. The processor 204 is configured to access a memory 212 having a tangible, non-transitory storage medium on which processor-executable instructions are embodied. The processor-executable instructions may define one or more programs configured to be executed by the processor 204. The one or more programs may include instructions configured to perform one or more of the operations or functions described herein with respect to the wearable device 100, 150, 170, 190. For example, the instructions may be configured to control or coordinate one or more communication channels and collect data from the plurality of sensors, perform signal processing, communicate with external devices, and control the overall operations of the wearable device, within the scope of the present disclosure.

The memory 212 can further store electronic data that can be used by the wearable device 100, 150, 170, 190. For example, the memory 212 can store electrical data such as timing and control signals or data for various modules, data structures or databases. The memory 212 can be any type of memory, for example, the memory 212 can be implemented as a read only memory (ROM), electrically erasable programmable read only memory (EEPROM) and/or random-access memory (RAM). One skilled in the art may also select other suitable types of technology for the memory 212, as desired.

In one non-limiting example, the processor 204 comprises a memory 212 that includes a non-transitory computer readable storage medium that stores a program configured to be executed by the processor 204. The program comprises instructions, which when executed by the processor 204 causes the wearable device 100, 150, 170, 190 to: i) receive physiological measurements representative of an internal load of the user detected by skin temperature sensor and/or a ECG sensor; ii) receive biomechanical measurements representative of an external load of the user detected by the ambient temperature sensor and/or the accelerometer; and iii) determine at least one metric indicative of the users health and/or performance.

The at least one wireless communication protocol 206 is adapted to provide communication between the processor 204, by way of the transmitter, receiver, or transceiver, and an external device, such as a mobile phone, computer, tablet, or the like. The at least one wireless communication protocol 206 may be configured to transmit and receive data or signals that may be interpreted by the instructions on the processor 204. In a specific example, the wearable device 100, 150, 170, 190 communicates with an external device using Bluetooth Low Energy Protocol (BLE). However, it should be appreciated that one skilled in the art may use other wireless communication protocols, such as for example, ANT, Zigbee, LoRa and/or LoRaWAN, while remaining within the scope of the present disclosure.

The battery 214 is adapted to store and provide power to the components of the wearable device 100, 150, 170, 190. The battery 214 may be a rechargeable power supply configured to provide power to the wearable device while it is being worn by the user. The wearable device 100, 150, 170, 190 may be configured to recharge the battery 214 using wireless charging via an external charging pack to let users recharge the wearable device without taking it off. As such, the wearable device 100, 150, 170, 190 includes a power management system 216 that receives power from an external device, such as for example an external charging pack, and is configured to deliver power to the electronic components 106, including the battery 214.

As discussed above, the wearable device 100, 150, 170, 190 may be made of a water-resistant material that allows the wearable device 100 to be durable and flexible enough to withstand active athletic use for a significant amount of time. To maintain a fully waterproof wearable device, the charging pack and wearable device 100, 150, 170, 190 are equipped with wireless charging capabilities.

Referring to FIG. 18, the processor 204 may operate in various modes, as defined by the processor-executable instructions on the memory 212, and based on a status of the wearable device 100, 150, 170, 190, such as, for example, power level status of the battery 214 and/or a status of a connection with an external device. Non-limiting examples of different operating modes may include:

A. Low Power "Shutdown" Mode 218.

When the processor 204 detects the battery 214 is running out of power, the processor 204 will initiate Low Power "Shutdown" Mode to preserve as much power as possible until the battery 214 is recharged. This mode protects the battery 214 from degradation. In this mode, the plurality of sensors 108 are disconnected from the power supply, no wireless communication is available, and the processor 204 will enter a "sleep" mode where the processor operates simply to occasionally check if the battery has been recharged.

B. No Wireless Connection, not Attached to User 220.

When the wearable device 100, 150, 170, 190 detects it is not attached to the user and there is no wireless connection to an external device, the wearable device will enter this mode. In this mode, the processor 204 disconnects a majority of the plurality of sensors 108 from the power supply, and occasionally checks if the wearable device has been attached to the user or if a wireless connection has been requested.

C. Not Attached to User, Wireless Connection 222.

When the wearable device 100, 150, 170, 190 establishes a wireless connection has been made while the wearable device is not attached to the user, the wearable device will communicate with the external device but readings from the plurality of sensors 108 must be manually requested by the external device. This mode is primarily used for testing, but it can also be used for DFU and collecting data saved from the memory 212.

D. Attached to User, No Wireless Connection 224.

When the wearable device 100, 150, 170, 190 detects it is attached to the user but there is no wireless connection to an external device, it enters this mode. In this mode, the processor 204 continuously reads data collected from the plurality of sensors, performs signal processing, and stores the processed signals in the memory 212 until a wireless connection is established.

E. Attached to User, Wireless Connection 226.

This is the normal operating mode for the wearable device. In this mode, the processor continuously reads data collected from the plurality of sensors 108, may perform signal processing, and streams the raw or processed data to the external device. The wearable device 100, 150, 170, 190 can also be updated through DFU in this state. In this state, any data stored in the memory 212 from a period without a wireless connection is simultaneously streamed to the connected external device.

F. Team Mode 228.

When the wearable device 100, 150, 170, 190 is worn by a group of users, the users have an option to form a team. When operating in a team mode, the wearable devices will form a mesh network. The mesh network transmits data from one device to another across the mesh to either a central collection and analysis location, such as an athletic trainer, coach, and/or team physician, or to one or more team members' individual mobile phone. This allows teams to compete or train together while still receiving continuous monitoring from the sidelines of a field without requiring members of the team to have their mobile devices with them.

Figure 1:
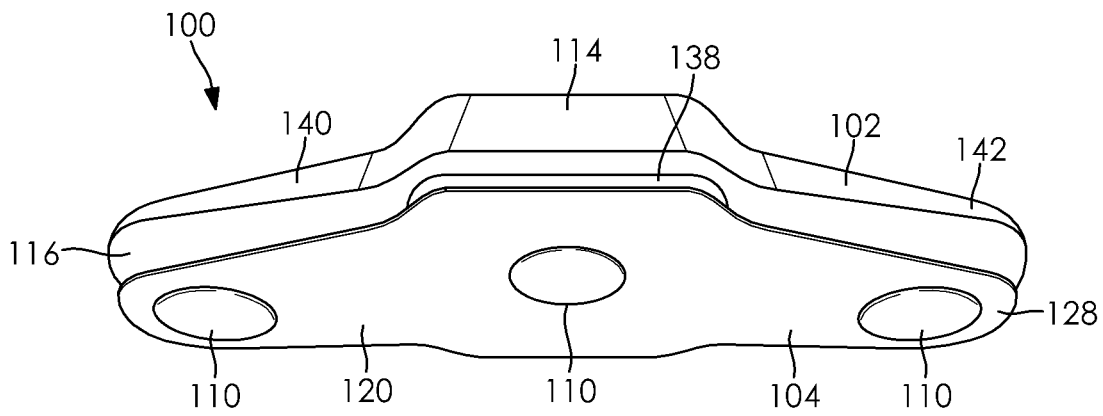
FIG. 1 is a bottom perspective view of a wearable device according to one embodiment of the present disclosure.
Figure 2:
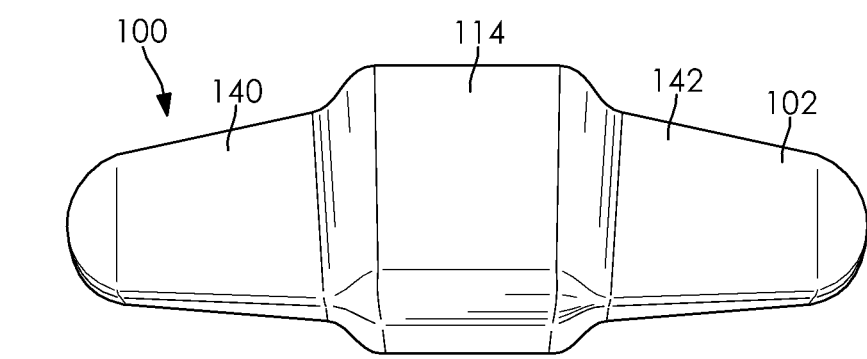
FIG. 2 is a top perspective view of the wearable device of FIG. 1.
Figure 3:
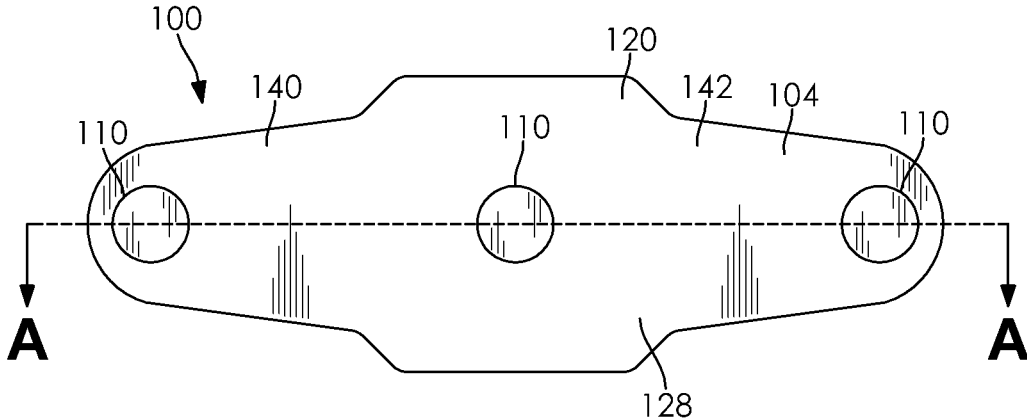
FIG. 3 is a bottom plan view of the wearable device of FIG. 1.

The ECG sensor 208 includes at least one electrode or contact 110 configured to detect electrical changes that are consequence of cardiac muscle depolarization followed by repolarization during each cardiac cycle. As shown in FIGS. 3-4, three electrodes or contacts 110 may be affixed to the lower side 120 of the primary electronics body 104 and placed in direct contact with the chest of the user when the wearable device 100 is attached. Cardiac related metrics such as heart rate (HR), resting heart rate (RHR), heart rate variability (HRV), and respiration rate (RR) are calculated through algorithms that first identify each ECG feature associated with ECG signal. The ECG features may include, but are not limited to, PQRST and U wave location, amplitude, phase and area, and time difference and length of all waves and wave complexes, for example, QRS, QT interval, and PQ interval, among others.

The HR, RHR, HRV, and RR may be calculated using just the R wave. For example, the HR is calculated in beats per minute (BPM) from the number of R waves recorded over time. RHR is calculated in BPM measured during certain stages of sleep when the user is inactive. HRV is calculated by recording the time in milliseconds between R waves and the average time variation between beats. RR is measured from the ECG signal due to Respiratory Sinus Arrhythmia.

The plurality of sensors 108 comprises a first temperature sensor 230 configured to measure a temperature of the skin of the user and a second temperature sensor 232 configured to measure a temperature of ambient air outside the wearable device 100, 150, 170, 190. As shown in FIGS. 4 and 11, the first temperature sensor 230 may be positioned directly above the skin of the user on the upper side 118 of the flexible primary electronics body 104 that forms the bottom of the wearable device 100, 150, 170, 190. In this example, a skin connection 234 may be made when the least one contact 110 touches the skin of the user. As a nonlimiting example, the at least one contact 110 may be a pad of copper printed on a bottom side 120 of the flexible PCB directly below the first temperature sensor 230 to facilitate heat transfer into the first temperature sensor 230.

As also shown in FIGS. 4 and 11, the second temperature sensor 232 may be connected to the wearable device 100, 150, 170, 190 by a long section of the flexible PCB 236 (FIG. 4). The second temperature sensor 232 may be positioned on a top side 238 of the long section of the flexible PCB 236, and a copper layer may be printed on a bottom layer of the long section of the flexible PCB 236 directly below the second temperature sensor 232 for increased heat transfer into the second temperature sensor 232. The long section 236 of the flexible PCB may be folded above the electronic components 106 on the upper side 118 of the flexible primary electronics body 104 and incorporated into the housing 102, for example, as shown in FIG. 4.

The first and second temperature sensors 230, 232 are configured to record and average values continuously and return a digital temperature measurement with accuracy. In a specific example, the first and second temperature sensors 230, 232 record and average values continuously over a 1 second sampling period and return a 16-bit resolution digital temperature measurement with better than ±0.1° C. accuracy.

The skin temperature measurements may be read directly from the wearable device 100, 150, 170, 190 and heat flux is measured through a comparison of skin and ambient temperature measurements, which has been surprisingly found to beneficially contribute to a more reliable and non-invasive prediction of core body temperature.

Referring to FIG. 11, the accelerometer 210 may be disposed near a center 240 of the flexible PCB or primary electronics body 192. The accelerometer 210 may be configured to measure acceleration forces acting on the user to determine the position, orientation and/or motion of the user. The accelerometer 210 can measure static acceleration forces, for example, gravitational force, and/or dynamic acceleration forces, for example, forces caused by movement or vibration of the accelerometer.

Although the wearable device 100, 150, 170, 190 is shown in FIG. 11 as having one accelerometer 210, it should be appreciated that more than one accelerometer or an array of multiple accelerometers may be employed to monitor acceleration at several locations on the wearable device while remaining within the scope of the present disclosure.

The accelerometer 210 can be an AC-response accelerometer (for example, charge mode piezoelectric accelerometer, voltage mode piezoelectric accelerometer), a DC-response accelerometer (for example, capacitive accelerometer, piezoresistive accelerometer), a microelectromechanical system (MEMS) accelerometer, or the like. The accelerometer can measure acceleration forces in one-dimension, two-dimensions, or three-dimensions. Any number of accelerometers can be used collect sufficient data to determine position and/or movement of the user while remaining within the scope of the present disclosure.

The accelerometer 210 can measure and output signals related to a linear acceleration of the user with respect to gravity along three axes. The first axis, or "roll," corresponds to a longitudinal axis of and/or extending through the body of the user, such as along a length and/or height of the user. Accordingly, the roll measurement can be used to determine whether the user is in a prone position, a supine position, or on a side. The second axis, or "pitch," of the accelerometer corresponds to the locations about the hip of the user, such as an axis extending between and/or through the hips of the user. The pitch measurement can be used to determine whether the user is sitting up or lying down. A third axis, or "yaw," of the accelerometer corresponds to a horizontal plane in which the user is located. The three axes that the accelerometer can measure linear acceleration are referred to as the X, Y, and Z axes.

In one specific example, the accelerometer 210 is a tri-axial accelerometer having a digital output that includes three signals representing measured acceleration along a particular axis. In this example, the output of the accelerometer is 16-bit, however, any sized output signal, such as for example 8-bit or 12-bit may be incorporated while remaining within the scope of the present disclosure. The range of acceleration measured is set from ±2 g to ±16 g.

The accelerometer 210 can be used to determine the position, orientation, and/or motion of the user, which allows for recording or calculating parameters such as impact forces, the number of steps the user takes, and an external workload via the rate of change of acceleration. The users step count can be used to measure other physical activities such as total calories burned, or distance covered. Furthermore, a motion profile of the user is important to the development of enhanced training programs that are tailored to specific goals of the user, such as an athlete, to maximize performance and reduce injury.

With renewed reference to FIGS. 14-15, a large number of physiological and biomechanical metrics are recorded or calculated from the data collected by the plurality of sensors, directly or indirectly through computations. The use of multiple sensors allows the wearable device to give a comprehensive detail about the health and fitness of the user.

Metrics directly recorded or calculated from data received by the plurality of sensors include direct ECG metrics, direct temperature metrics, and direct accelerometer metrics. Direct ECG metrics include HR, RR, HRV, RHR, ECG features, for example PQRST and U waves, and time difference and length of all waves and wave complexes. Direct temperature metrics includes skin temperature, ambient temperature, and heat flux. Direct accelerometer metrics include acceleration in X, Y, Z axes, impacts, steps, and external workload.

The above stated metrics can be combined to provide further physiological and biomechanical metrics to be recorded or calculated from the data collected by the plurality of sensors indirectly through computations. Non-limiting examples of indirect metrics include sleep detection and quality, activity, recovery, motion profiling, cardiovascular strain, internal workload, athletic performance, and core body temperature.

The sleep metrics are derived from HR, RR, acceleration, and temperature metrics. Activity metrics are derived from HR, acceleration, and temperature metrics. Recovery metrics are derived from HR and activity metrics. Motion profiling is derived from acceleration, cardiovascular strain and internal workload are derived from ECG metrics. Athletic performance is derived from internal workload and external workload.

Core body temperature is derived from HR, temperature, and heat flux. When core body temperature is paired with HR and ECG information, internal exertion can be calculated, which then allows user to measure how heat is getting dissipated. Predicting core body temperature lets a user know when their body temperature is approaching overheating.

In a further example, cardiovascular information, temperature information, and accelerometry can calculate how hard the internal body is working compared to how much work is being produced externally. When the two are compared, you can determine how much you respond to a certain level of external activity and quantify fitness objectively.

It has been advantageously found that the employment of the first temperature sensor for determining skin temperature, and the second temperature sensor for determining ambient air temperature, permits for the effective calculation of the core body temperature which, heretofore, was only able to be determined by invasive temperature probes. The employment of the biocompatible adhesive together with this unique use of temperature sensors, which serves to minimize loss of contact and undesirable shifting of the sensors, also facilitates this determination that was not otherwise known prior to the present disclosure.

While certain representative embodiments and details have been shown for purposes of illustrating the present disclosure, it will be apparent to those skilled in the art that various changes may be made without departing from the scope of the disclosure, which is further described in the following appended claims.

What is claimed is:

1. A wearable device for monitoring physiological and biomechanical parameters of a user, comprising:

a housing;

a primary electronics body disposed at least partly within the housing, the primary electronics body including a processor and having a flexible PCB portion and a rigid PCB portion, wherein the flexible PCB portion includes a first wing disposed on one side of the rigid PCB portion and a second wing disposed on the other side of the rigid PCB portion;

a biocompatible adhesive disposed on a bottom side of one of the housing and the primary electronics body and configured to be removably affixed to the user;

an electrocardiogram sensor in electrical communication with the processor, the electrocardiogram sensor configured to detect electrical changes of a heart of the user, wherein the processor is configured to calculate heart rate, respiration rate, resting heart rate, and heart rate variability from the electrical changes of the heart of the user;

a first temperature sensor in electrical communication with the processor, the first temperature sensor configured to continuously measure a first temperature, the first temperature being a temperature of skin of the user disposed adjacent to the first temperature sensor;

a second temperature sensor in electrical communication with the processor, the second temperature sensor configured to continuously measure a second temperature, the second temperature being a temperature of ambient air outside the wearable device;

at least one contact disposed on at least one of the first wing and the second wing, the at least one contact configured to contact skin of the user; wherein the contact is a copper pad printed on a bottom side of the flexible PCB directly below the first temperature sensor to facilitate heat transfer into the first temperature sensor, wherein the processor is configured to simultaneously and continuously monitor both the core body temperature of the user and one of the heart rate, respiration rate, resting heart rate, and heart rate variability from the electrical changes of the heart of the user and monitor for a change in the core body temperature of the user over time.

2. The wearable device of claim 1, further comprising an accelerometer attached to the primary electronics body and in electrical communication with the processor, wherein the accelerometer is configured to determine at least one of a position, orientation, and motion of the user.

3. The wearable device of claim 2, wherein the processor is configured to calculate impact forces, a number of steps taken, and an external workload via a rate of change of acceleration of the user.

4. The wearable device of claim 1, further comprising an accelerometer and an electrocardiogram sensor attached to the primary electronics body and in electrical communication with the processor, wherein the accelerometer is configured to determine at least one of a position, orientation, and motion of the user, and wherein the electrocardiogram sensor is configured to detect electrical changes of a heart of the user.

5. The wearable device of claim 4, wherein the processor is configured to calculate the physiological and biomechanical parameters from data collected by the accelerometer and the ECG sensor.

6. The wearable device of claim 1, wherein the primary electronics body is one of a fully flexible circuit board and a fully rigid circuit board.

7. The wearable device of claim 1, wherein the biocompatible adhesive is a silicone-acrylate-based adhesive.

8. A wearable device for monitoring physiological and biomechanical parameters of a user, comprising:

a housing;

a primary electronics body disposed at least partly within the housing, the primary electronics body including a processor, and having a flexible PCB portion and a rigid PCB portion, wherein the flexible PCB portion includes a first wing disposed on one side of the rigid PCB portion and a second wing disposed on the other side of the rigid PCB portion;

an electrocardiogram sensor in electrical communication with the processor, the electrocardiogram sensor configured to detect electrical changes of a heart of the user, wherein the processor is configured to calculate heart rate, respiration rate, resting heart rate, and heart rate variability from the electrical changes of the heart of the user;

a first temperature sensor in electrical communication with the processor, the first temperature sensor configured to measure a first temperature, the first temperature being a temperature of skin of the user disposed adjacent to the first temperature sensor;

a second temperature sensor in electrical communication with the processor, the second temperature sensor configured to measure a second temperature, the second temperature being a temperature of ambient air outside the wearable device, at least one contact disposed on at least one of the first wing and the second wing, the at least one contact configured to contact skin of the user; wherein the contact is a copper pad printed on a bottom side of the flexible PCB directly below the first temperature sensor to facilitate heat transfer into the first temperature sensor, and a biocompatible adhesive disposed on a bottom side of one of the housing and the primary electronics body and configured to be removably affixed to the user, wherein the biocompatible adhesive is a silicone-acrylate-based adhesive,

wherein the processor continuously calculates core body temperature of the user and monitors for a change in the core body temperature of the user over time, wherein each of the first temperature sensor and the second temperature sensor are configured to record and average values continuously while the primary electronics body is removably affixed to the user to provide calculation of the core body temperature non-invasively and continuously, and wherein the processor is configured to simultaneously and continuously monitor both the core body temperature of the user and one of the heart rate, respiration rate, resting heart rate, and heart rate variability from the electrical changes of the heart of the user.

9. The wearable device of claim 8, further comprising an accelerometer attached to the primary electronics body and in electrical communication with the processor, wherein the accelerometer is configured to determine at least one of a position, orientation, and motion of the user.

10. The wearable device of claim 9, wherein the processor is configured to calculate impact forces, a number of steps taken, and an external workload via a rate of change of acceleration of the user.

11. The wearable device of claim 8, further comprising an electrocardiogram sensor in electrical communication with the processor, the electrocardiogram sensor configured to detect electrical changes of a heart of the user, wherein the processor is configured to calculate heart rate, respiration rate, resting heart rate, and heart rate variability from the electrical changes of the heart of the user.

12. The wearable device of claim 8, further comprising an accelerometer and an electrocardiogram sensor attached to the primary electronics body and in electrical communication with the processor, wherein the accelerometer is configured to determine at least one of a position, orientation, and motion of the user, and wherein the electrocardiogram sensor is configured to detect electrical changes of a heart of the user.

13. The wearable device of claim 12, wherein the processor is configured to calculate the physiological and biomechanical parameters from data collected by the accelerometer and the ECG sensor.

14. The wearable device of claim 8, wherein the primary electronics body is one of a fully flexible circuit board and a fully rigid circuit board.

15. A wearable device for monitoring physiological and biomechanical parameters of a user, comprising:
   a housing;
   a primary electronics body disposed at least partly within the housing and having a flexible PCB portion and a rigid PCB portion, wherein the flexible PCB portion includes a first wing disposed on one side of the rigid PCB portion and a second wing disposed on the other side of the rigid PCB portion;
   a plurality of electronic components electrically connected to the primary electronics body, the plurality of electronic components including:
      a memory having a tangible, non-transitory storage medium on which processor-executable instructions are embodied,
      a processor in electrical communication with the memory and configured to execute the processor-executable instructions of the memory,
      a first temperature sensor in electrical communication with the processor, the first temperature sensor configured to continuously measure a first temperature, the first temperature being a temperature of skin of the user disposed adjacent to the first temperature sensor;
      a second temperature sensor in electrical communication with the processor, the second temperature sensor configured to continuously measure a second temperature, the second temperature being a temperature of ambient air outside the wearable device,
      wherein each of the first temperature sensor and the second temperature sensor are configured to record and average values continuously while the primary electronics body is removably affixed to the user to provide calculation of a core body temperature non-invasively and continuously;
      at least one contact disposed on at least one of the first wing and the second wing, the at least one contact configured to contact skin of the user; wherein the contact is a copper pad printed on a bottom side of the flexible PCB directly below the first temperature sensor to facilitate heat transfer into the first temperature sensor,
      an electrocardiogram sensor in electrical communication with the processor, the electrocardiogram sensor configured to detect electrical changes of a heart of the user, wherein the processor is configured to calculate heart rate, respiration rate, resting heart rate, and heart rate variability from the electrical changes of the heart of the user; and
      an accelerometer in electrical communication with the processor, wherein the accelerometer is configured to determine at least one of a position, orientation, and motion of the user; and
   a biocompatible adhesive disposed on a bottom side of one of the housing and the primary electronics body and configured to be removably affixed to the user, wherein the biocompatible adhesive is a silicone-acrylate-based adhesive
   wherein the processor is configured to:
      simultaneously receive data from the first temperature sensor, the second temperature sensor, the electrocardiogram sensor, and the accelerometer,
      continuously calculate at least one physiological and biomechanical metric from the data received,
      output at least one metric indicative of a core temperature of the user, and
      monitors for a change in the core body temperature of the user over time.

16. The wearable device of claim 1, wherein the processor is configured to continuously compare the core body temperature of the user in relation to measured physiological and biomechanical measurements.

17. The wearable device of claim 1, wherein:
   the housing defines a shape corresponding to the primary electronics body and includes a first housing wing and a second housing wing corresponding to the first and second wings of the primary electronics body;
   each of the first and second wings defines an opening having the at least one contact placed adjacent thereto;
   the second temperature sensor is connected to the wearable device by a long section of flexible PCB and is positioned on a top side of the long section of the flexible PCB;
   a copper layer is printed on a bottom layer of the long section of the flexible PCB directly below the second temperature sensor for increased heat transfer into the second temperature sensor; and the biocompatible adhesive defines at least one opening having a geometric shape corresponding to that of the at least one contact.

18. The wearable device of claim 1, further comprising:

an analytical software platform configured to perform data collection, signal processing, and use of early detection algorithms to calculate the probability of infections;

Long Short-Term Memory (LSTM) networks configured to facilitate recognition of long term dependencies and assist in predicting outcomes of time dependent data; and wherein the processor is configured to derive sleep metrics from heart rate, respiration rate, acceleration, and temperature metrics, and derive activity metrics from heart rate, acceleration, and temperature metrics.

19. The wearable device of claim 1, wherein the processor is configured to operate in a team mode where multiple wearable devices form a mesh network that transmits data from one device to another across the mesh to a central collection and analysis location.

20. The wearable device of claim 18, wherein the mesh network transmits data from one device to another across the mesh to one or more mobile phones of individual team members.

\* \* \* \* \*